US007225812B2

(12) United States Patent
Nedeljkovic et al.

(10) Patent No.: US 7,225,812 B2
(45) Date of Patent: Jun. 5, 2007

(54) DEVICE FOR NEUTRALIZING ELECTROMAGNETIC RADIATION

(76) Inventors: Voislav Nedeljkovic, Brdjanska 144, Beograd, Ripanj (YU) 11232; Petar Nedeljkovic, Brdjanska 144, Beograd, Ripanj (YU) 11232

( * ) Notice: Subject to any disclaimer, the term of this patent is extended or adjusted under 35 U.S.C. 154(b) by 467 days.

(21) Appl. No.: 10/490,758

(22) PCT Filed: Aug. 3, 2001

(86) PCT No.: PCT/YU01/00019

§ 371 (c)(1), (2), (4) Date: Mar. 24, 2004

(87) PCT Pub. No.: WO03/006105

PCT Pub. Date: Jan. 23, 2003

(65) Prior Publication Data

US 2004/0231680 A1 Nov. 25, 2004

(51) Int. Cl.
*A61B 19/00* (2006.01)
*A61B 17/52* (2006.01)
*A61N 2/00* (2006.01)

(52) U.S. Cl. .......................................... 128/897; 600/9

(58) Field of Classification Search .............. 600/9–15; 128/897–899
See application file for complete search history.

(56) References Cited

U.S. PATENT DOCUMENTS 5,632,720 A * 5/1997 Kleitz ......................... 601/15

FOREIGN PATENT DOCUMENTS

| | | |
|---|---|---|
| DE | 32 20 565 | 12/1983 |
| DE | 33 41 756 | 5/1985 |
| FR | 2 667 435 | 9/1990 |
| WO | WO 92/12682 | 8/1992 |
| WO | WO 98/06453 | 2/1998 |
| WO | WO 00/25857 | 5/2000 |
| WO | WO 01/19451 | 3/2001 |
| WO | WO 01/19451 A1 * | 3/2001 |

OTHER PUBLICATIONS

International Search Report, Apr. 3, 2002.

* cited by examiner

*Primary Examiner*—Charles A. Marmor, II
*Assistant Examiner*—Sara Lustusky
(74) *Attorney, Agent, or Firm*—Carlson, Gaskey & Olds, PC

(57) ABSTRACT

A neutralizer for electromagnetic radiation, particularly harmful radiation, caused by electro-magnetic fields from electric lines, installations, machines, appliances and apparatus includes a cylindrical body (1) with a semi-circular external groove (2) and two cylindrical chambers (4). A bar core (5) in the chambers (4) has solenoids (S) rotatably mounted thereon. Chambers (4) are hermetically closed by thread plugs (6). The difference in electrical potentials between the body (1) and the solenoid (S) causes a weak electric field of high frequency that annuls the effect of technical radiation in its environment.

8 Claims, 2 Drawing Sheets

A 1 S 12 11 111 SPS US 2 41 4 S 6 43 42 3 SRS 4 5

DEVICE FOR NEUTRALIZING ELECTROMAGNETIC RADIATION

THE FIELD OF THE INVENTION

The subject of the invention in general relates to the field of human necessities in the domain of medical sciences and it particularly refers to a neutralizer for electromagnetic radiation.

According to the International Patent Classification (IPC), the subject of the invention is set down as classification symbol A 61 N 1/16 that refers to electrotherapy for the purpose of protecting or neutralizing the noxious influences of atmospheric or earthly radiation.

TECHNICAL PROBLEM

This invention provides a device that neutralizes harmful electromagnetic radiation caused by electromagnetic fields of electric lines, installations, machines, devices and various electrical appliances, thereby improving considerably the quality of life and the health of people both in their working premises and space of life.

PRIOR-ART

Nowadays, there are a lot of differently constructed devices for elimination and blockade of harmful electromagnetic radiation, that are based on the radiation of particularly formed natural materials, together with using the latest achievements in the field of electronics, where all these devices are intended for broad application in public, working and residential buildings.

In Yugoslav patent file No 48657, described and shown is an absorbent inset for removing electric and magnetic radiation, having two threads around its inset with the form of standard coils that are intercrossed. Both threads are wound up the same middle part axis in the same direction, one onwards, the other backwards. The ends of the conductor are coupled by conductive link, while the bent conductor is encircled by threads. The device functions in such a manner that by two double threads it brings to the absorption of two opposite electric and magnetic field for generating the currents in its coils. Induced current in one thread is equal with that in the other thread, herewith these oppositely directed currents are mutually annulled. The final effect of the influence of the device is in the consumption of both the energy of electric field and the other of magnetic field. In the German patent application DE 32 20 565 (A1), an electric device is described and shown that produces an electromagnetic field opposite to the pathogenic electromagnetic field. This device solves the problem of electric and magnetic field, as well, that has harmful consequences and its constant feeding into electric energy is required for its operation.

In German patent application DE 33 41756 (A1) is described and shown a blanket with metal filaments for the protection of electric and magnetic field, but the effect is narrowly limited only to the space of bed, i.e. couch.

Bioenergetic reequalizer is described in the Yugoslav patent application P-899/92 and explained as energetic transceiver for absorption and removing all harmful and destructive radiation towards the human organism. Also, in Yugoslav patent applications P-2154/90 and P-2155/90 are described a Neutralizer for harmful radiation (having the ring form and nails arranged in multicomponent mass that is inserted in the box) and Leadout of harmful radiation (having the socket that is cable connected to the spiral put in mass existing in the box).

However, all the above mentioned known solutions have their imperfections compared to here suggested Neutralizer for electromagnetic radiation. These imperfections are obvious in the complexity of their construction on one side and, on the other side, in simple, very narrow, field of application. Besides, some devices are to be fed by electric current which is additional complication. Further imperfections of certain known devices is that they are of no influence to properly functioning of flora and fauna (animals and plants).

Analyzing the imperfections of already existing solutions, the inventors came to the specific but, in the very nature, simple solution for a neutralizer for electromagnetic radiation that is to be further described and shown in drawings.

SUMMARY OF INVENTION

The sources of harmful radiation, unperceivable to common perception are very often developers of biological and psychological damages. Those types of radiation are unperceivable, but have extremely dangerous influence on health, vitality, behavior and temper, and therefore for the happiness and destiny of people. These influence vibratory rhythm of living cells, changing their polarity and causing imbalance of energy that often brings to some illnesses.

Being in an urban environment, particularly in big cities, derange natural life conditions and people are exposed to manifold sources of harmful radiation. These, so called technical radiation are induced by electromagnetic waves of different frequencies caused by electric lines of high and low voltage, transformer substations, electric systems, electrical machines and apparatus, household appliances, radio and TV sets, (personal) computers and so like. Of course, all harmful influences cannot be eliminated completely, but so far research has proved that there are ways to approach the elimination and blockade of harmful radiation.

A neutralizer for electromagnetic radiation according to this invention is produced of metal in the form of cylindrical body, having a central external groove and two cylindrical chambers in which, over the bar core wire solenoids are made of other precious metal and are freely moved up. Both chambers are on the enlarged ends hermetically housed by thread plugs.

The difference in electric potentials between the body and solenoids causes a weak electric field of high-frequency that annuls the effect of low-frequency technical radiation in the environment.

The above benefits are achieved by a novel construction of a neutralizer. For example, on the cylindrical body there are concentric disks having integrally formed outer rings, while between disks, inner rings protrude integrally from the body. The external diameter of the disks is greater than the external diameter of the inner rings. This is the first novel characteristic of the neutralizer.

The second novelty is in solenoids that include an internal spiral around which is integrally in opposite direction, wound up the middle spiral. At the end, in the directions of inner spiral, both spirals are integrally wound up by the same wire. In that way, solenoid includes three uninterrupted cylindrical springs, one in another. It is important to point out that solenoids in cylindrical chambers are freely movable around the bar core between the tread plugs. The neutralizer is dimensioned so that, when used by people, it can be held on the chests, in pocket, or as pendant. In that case, the neutralizer is fed by human biofield, producing around the body types of energies not preventing the exchange of energies between the source of noxious radiation and individuals exposed to the radiation. Because of that fact the negative response of the neurovegetative system fade away or appear in a significantly soothing extent.

By using the neutralizer, an improved ability to work is maintained. Rest in the zones of biophysical effect is even better. It can be used in personal protection of individuals from harmful radiation in working premises, at home, and out of doors, on a beach, on an excursion and so like. Along with expert estimation of circumstances, the neutralizer can be successfully used even for the protection of flats, apartments and nature from harmful electromagnetic radiation. Furthermore it can be used in orchards, gardens and flower alleys, as well as in barns and poultry houses in order to improve productivity by proper arrangement of neutralizer.

Other examples include computer centers, air flight control towers, radar set crews, boats, trolleybuses, telephone operating rooms, control panels in factories, and military vehicles, cranes and so on.

In a word, opportunities for all practical purposes in applying neutralizer according to this invention are unlimited.

BRIEF DESCRIPTION OF THE DRAWINGS

For the purpose of easier understanding and for presentation of its realization in practical experience, the drawings enclosed with the application refer to the neutralizer of electromagnetic radiation, and where.

DETAILED DESCRIPTION OF INVENTION

Figure 3:
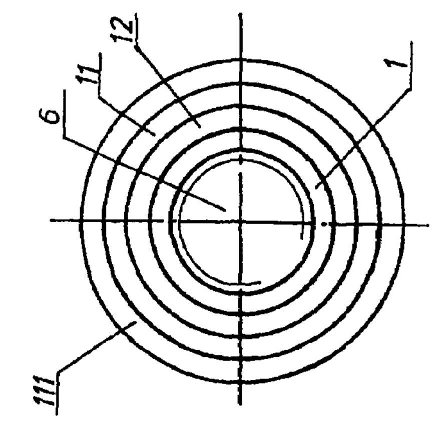
FIG. 3 represents side view of the neutralizer as seen in the direction of arrow P, from FIG. 1.
Figure 1:
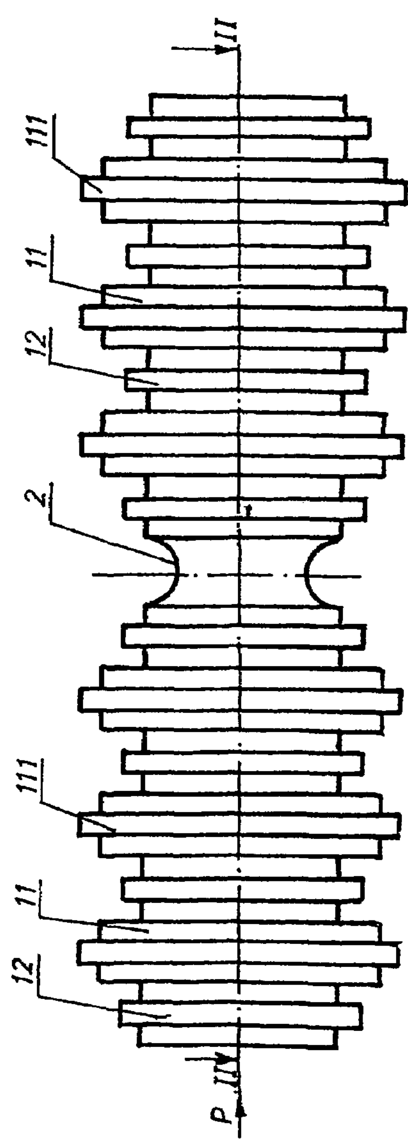
FIG. 1 represents an exterior view of the neutralizer.
Figure 2:
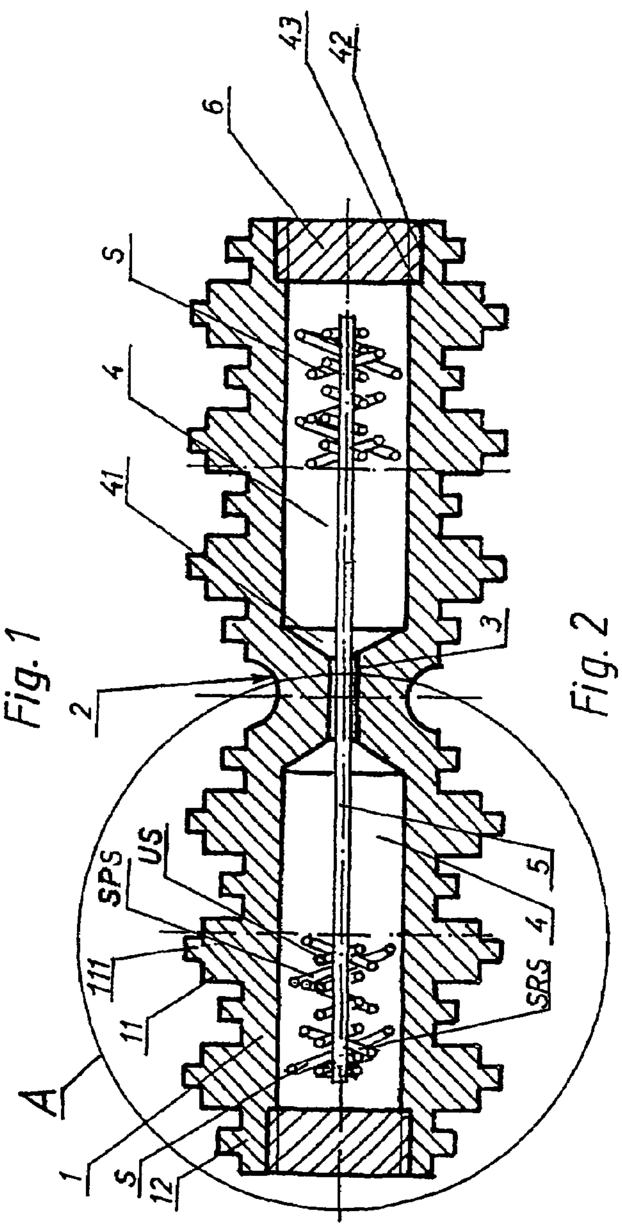
FIG. 2 represents the view of longitudinal cut of the neutralizer taken along the line II—II as in FIG. 1.
Figure 4:
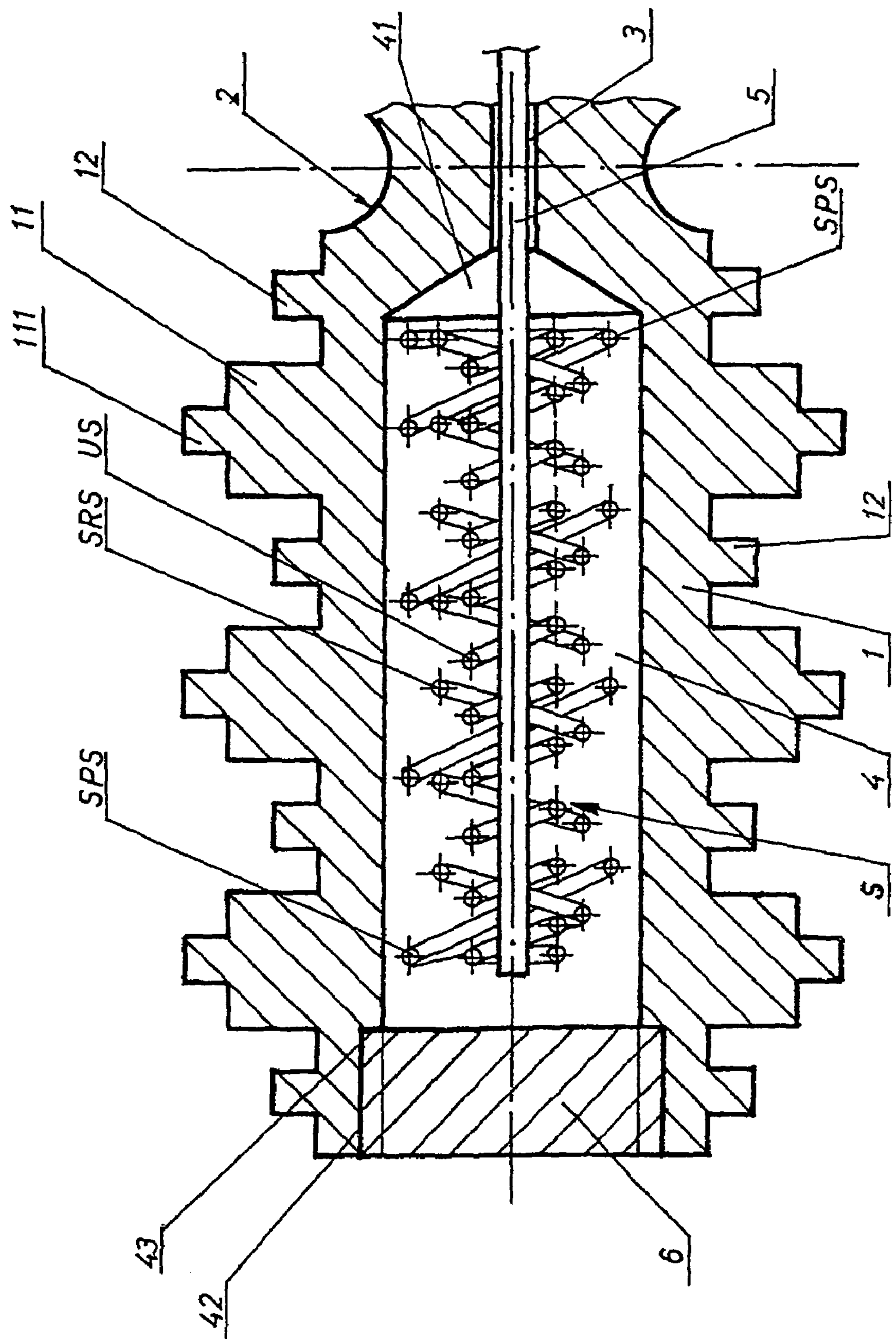
FIG. 4 represents an enlarged view of detail “A” from FIG. 2.

Referring to the FIGS. 1–4, it can be seen that the neutralizer for electromagnetic radiation, includes a cylindrical body 1, which has integral outwardly protruding and mutually parallel and symmetrically detached concentric disks 11. Outer rings 111 are integral with and protrude outwardly from the symmetric middle of each disk 11. In the middle between the disks 11 on the cylindrical body 1 are symmetrically protruded inner rings 12, which are also integral with the cylindrical body 1. The external diameter of the rings 12 is less than the diameter of the disks 11, and those are concentric with cylindrical body 1.

In the middle of the length on cylindrical body 1, a semi-circular groove 2 is externally cut By its axis of symmetry, the groove 2 effectively divides cylindrical body 1 into two identical halves.

In the central part inside cylindrical body 1 a short connecting canal 3 is coaxial and symmetrical. The canal 3 is in connection to cylindrical chambers 4 through funnel like enlargements 41 on opposite ends of the canal 3. The other ends of the cylindrical chambers 4 are extended by cylindrical thread enlargements 42, that are intended for thread plugs 6. Thread plugs 6 can be without threads and thus, by packing into enlargements 42 without thread, all up to ring-like support 43, a hermetically closed structure is achieved.

Before setting thread plugs 6, a bar core 5, whose length comes close to both enlargements 42, is pulled through connecting canal 3. Around bar core 5, in both cylindrical chambers 4, solenoids S are freely circled.

Solenoids S are done so that inner spiral US is first wound up, and then from the same wire in the opposite direction, externally around inner spiral US, middle spiral SRS is wound up, so as to wind the widest external spiral SRS around them and in the direction of inner spiral US. The neutralizer for electromagnetic radiation is made of different metals, where cylindrical body 1 is made of one type of metal and bar core 5 and solenoid S are made of other ingot. Considering the fact that solenoids S can be freely moved in their cylindrical chambers 4 and along bar core 5, it can be said that such a neutralizer represents a mechanical oscillator circuit, too.

The difference between electrical potentials of the cylindrical body 1 and the solenoids S generates a weak electric field of high frequency, that annuls the effect of natural and technical radiation of lower frequencies, generating in such a way beneficial radiation in the environment, which is the real aim. At the end, looking at FIGS. 1 and 2 of the drawings, it can be seen that the construction of the neutralizer for electromagnetic radiation, according to this invention has a novelty in that, that compared to longitudinal and vertical axis of symmetry it is fully symmetrical.

Industrial and Other Application of Invention

The manner of application of this invention is set forth in the description and therefore needs no particular description. All the above mentioned is checked and particularly experienced by using manufactured samples.

The invention claimed is:

1. A neutralizer for electromagnetic radiation comprising:

a cylindrical body having a plurality of concentric disks, each of the disks having a ring protruding therefrom, the cylindrical body including two chambers formed therein and a canal connecting the two chambers;

a bar core disposed inside the chambers and the canal; and solenoids formed around the bar core in the chambers.

2. The neutralizer of claim 1 further including a plurality of inner rings protruding from the body between the disks.

3. The neutralizer of claim 2 wherein the external diameter of the disks is greater than the external diameter of the inner rings.

4. The neutralizer of claim 2 wherein the body further includes a semi-circular groove generally aligned with the canal.

5. The neutralizer of claim 2 further including funnel-shaped portions connecting the canal to the two chambers.

6. The neutralizer of claim 1 further including a threaded plug closing an outer end of one of the chambers.

7. The neutralizer of claim 1 wherein the solenoids are rotatably mounted on the bar core.

8. The neutralizer of claim 1 wherein each solenoid includes an inner spiral wound in a first direction, a middle spiral wound in a section direction opposite the first direction and an outer spiral wound in the first direction.

* * * * *